US005722415A

United States Patent [19]
Rom et al.

[11] Patent Number: 5,722,415
[45] Date of Patent: Mar. 3, 1998

[54] CONTINUOUS CARDIAC OUTPUT MONITOR

[75] Inventors: Paul F. Rom, Kentwood; Russell A. Corace, Grand Rapids, both of Mich.

[73] Assignee: Medtronic, Inc., Minneapolis, Minn.

[21] Appl. No.: 640,322

[22] Filed: Apr. 30, 1996

[51] Int. Cl.$^6$ ................................................. A61B 10/00
[52] U.S. Cl. ........................................ 128/713; 128/662.03
[58] Field of Search ........................ 128/662.06, 661.08, 128/672, 662.03, 129, 713

[56] References Cited

U.S. PATENT DOCUMENTS

| | | | |
|---|---|---|---|
| 3,216,424 | 11/1965 | Chardack | 607/129 |
| 4,671,295 | 6/1987 | Abrams et al. | |
| 4,722,347 | 2/1988 | Abrams et al. | |
| 5,205,292 | 4/1993 | Czar et al. | |
| 5,284,146 | 2/1994 | Czar et al. | |
| 5,469,853 | 11/1995 | Law et al. | 128/662.06 |

OTHER PUBLICATIONS

"New. Continuous Cardiac Output. Now.," Product Brochure, 2 pages, Apr. 1993.
"XEMEX® Thermodilution and Wedge Pressure Catheters.," Product Brochure 2 pages, undated.

*Primary Examiner*—Scott Getzow
*Attorney, Agent, or Firm*—Foley & Lardner

[57] ABSTRACT

A device for continuously monitoring the output of a heart in a surgical patient includes a probe head attached at one end to a catheter adapted to be inserted into the patient. The probe head includes a probe and a pair of flexible flat projections extending outwardly from opposite sides of the probe for securing the probe head in the transverse sinus of the patient. At least one transducer is positioned in the probe for detecting a condition of the heart. A hollow needle is adapted for receiving the probe head prior to its installation in the patient, such that the probe head can be installed in the patient immediately after mediansternotomy and division of the patient's pericardium by inserting the needle through the patient's chest wall. A method for continuously monitoring the condition of the heart in a surgical patient includes the steps of providing a probe head responsive to heart function; positioning the probe head in the transverse sinus of the patient proximal to the aortic valve and behind the ascending aorta; and displaying an output of the probe head reflective of the heart condition.

15 Claims, 2 Drawing Sheets

CONTINUOUS CARDIAC OUTPUT MONITOR

BACKGROUND OF THE INVENTION

1. Field of the Invention

This invention relates to cardiac monitoring, and more particularly to a method and device for monitoring the output of a heart during post operative open heart surgery.

2. Description of the Related Art

Cardiac output monitoring has been performed on most open heart surgery patients since the development of the intravascular thermodilution (T-D) cardiac output catheter over 20 years ago. The Swan-Ganz catheter is one form of a T-D style catheter and is the current standard for cardiac output measurement. T-D style catheters are positioned intravascular, typically inserted into the jugular vein and threaded into the heart. Such a catheter calculates estimated cardiac output intermittently by measuring externally induced fluid temperature differentials within the pulmonary artery (on the right side of the heart) to measure flow velocity during the cardiac cycle and then assuming the value is indicative of left side heart function. The flow velocity is determined by calculating an average for 3–4 temperature inducements over a 4–5 minute period.

The use of T-D catheters is subject to many variables including operator error, injectate temperature variances, speed and timing of the cold fluid injection, etc. Although not accurate in measurement, the values generated by this technique are generally and historically accepted as a relative depiction of cardiac performance.

Besides their measurement inaccuracy, which is estimated at ±20%, T-D catheters currently in use are relatively expensive and are not innocuous. The medical literature has documented the side effects and complications associated with these intravascular catheters in great detail. Among the more serious complications are pulmonary artery rupture, increased infection rate, arrhythmias, difficult insertion and removal resulting in catheter body knotting or catheter balloon rupturing, intracardiac trauma to valves and ventricles, cardiac perforation, high risk of fluid overload, etc.

A recent improvement is a "continuous output" T-D catheter that features a modified Swan-Ganz design by adding an electrical temperature filament to the distal end of the catheter. It induces electrically generated temperature differentials into the fluid path thereby eliminating the need to inject a cold solution into the blood stream. This device reads the subtly induced temperature changes in the fluid path during the cardiac cycle to calculate flow velocity. The eventual readout is an average reading of data gathered over a 30 second to one minute interval.

As described in U.S. Pat. No. 4,671,295, it is known to use a pair of Doppler crystals for measuring volumetric blood flow in the aorta. The Doppler crystals also measure the changes in aortic diameter with each beat of the heart.

Other techniques occasionally reported for use in monitoring continuous cardiac output include Trans Esophageal Echocardiographic measurement (TEE) and the IQ System (Renaissance Technologies, Newton, Pa.), which employ thoracic electrical impedance measurement and time-frequency signal processing to compute cardiac output.

There exists a continuing need for a more accurate, cost-effective, and continuous output-type catheter for perioperative cardiac management. The present invention substantially fulfills that need.

SUMMARY OF THE INVENTION

These and other problems of the prior art are overcome by the provision of a device for continuously monitoring the output of a heart in a surgical patient. According to one aspect of the invention, a probe head associated with one end of a catheter is adapted for insertion into a patient. The probe head includes a probe and a pair of flexible flat projections extending outwardly from opposite sides of the probe for securing the probe head in the transverse sinus of the patient. At least one transducer is positioned in the probe for detecting a condition of the heart.

According to another aspect of the invention, a hollow needle is adapted for receiving the probe head prior to installing the probe head in the patient, such that the probe head can be installed in the patient immediately after medianasternotomy and division of the patient's pericardium by inserting the needle through the patient's chest wall.

According to one feature of the invention, a method for continuously monitoring the condition of the heart in a surgical patient includes the steps of providing a probe head responsive to heart function; positioning the probe head in the transverse sinus of the patient proximal to the aortic valve and behind the ascending aorta; and displaying an output of the probe head reflective of the heart condition.

According to a further feature of the invention, a method for continuously monitoring the condition of the heart includes the provision of a probe head that is capable of monitoring both the blood centerline velocity of the aorta and changes in the aortic diameter in real time.

According to an even further feature of the invention, the probe head is secured to the transverse sinus with releasable sutures, and the catheter body is secured at a position distal from the heart with absorbable sutures.

BRIEF DESCRIPTION OF THE DRAWINGS

The invention will now be described with reference to the drawings in which.

DETAILED DESCRIPTION OF THE PREFERRED EMBODIMENTS

Figure 1:
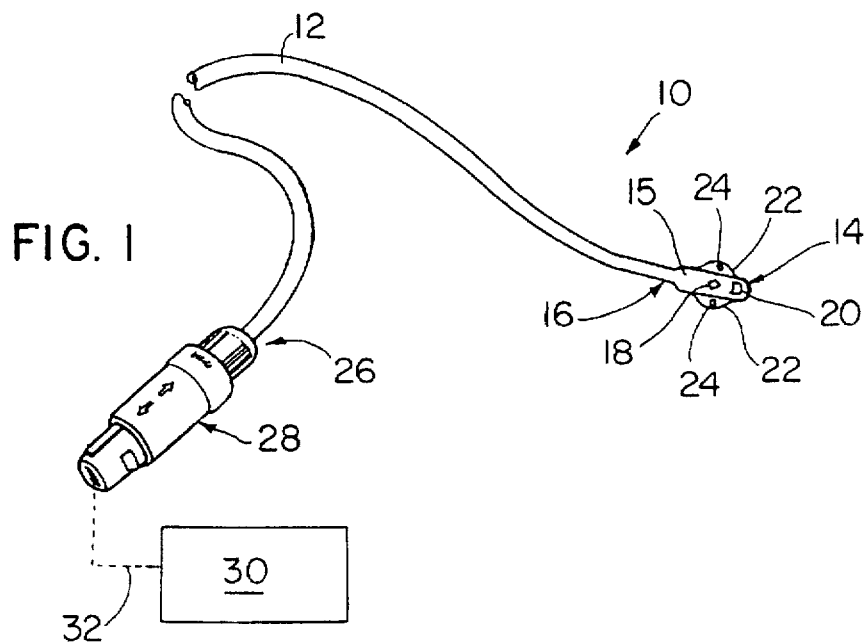
FIG. 1 is a perspective view of a cardiac monitoring catheter according to the invention.

Referring now to FIG. 1, the cardiac monitoring catheter 10 comprises a small, elongated flexible body 12 having a distal end 16 which terminates at a probe head 14. The probe head 14 comprises a probe 15 and a pair of flexible flat wings 22 that project outwardly from opposite sides of the probe 15. A pair of Doppler crystals 18, 20 are impregnated into the probe 15. One of the crystals measures the center line velocity of the blood passing through the aorta while the other crystal measures changes in the aortic diameter with each beat of the heart. The wings, together with the probe, form a cobra head-shaped structure. Each wing 22 features a tiny suture port 24 for receiving at least one suture to anchor the probe head 14 against movement once positioned in the body of a patient. The overall length of the catheter 10 is preferably 24 inches. However, the catheter may be sized in other lengths depending on individual requirements of the patient.

A proximal end 26 of the wire 12 terminates in a standard dual coaxial electro-mechanical connector 28 that interfaces with a monitor 30. Suitable electrical signal conduits extend between the Doppler crystals 18, 20 and the connector 28. The monitor 30 is preferably a backlit liquid crystal display. A reusable (sterilizable) extension cable 32 (shown in dashed line) is used to interconnect the connector 28 and the monitor 30. The monitor 30 is associated with well-known circuitry (not shown) for energizing each Doppler crystal and for interpreting each crystal's response. The monitor may be positioned at the head of the surgical table for anesthesia access or positioned at the patient's bedside in the intensive care unit. The monitor may provide data parameter readouts in the form of multiple display options such as continuous cardiac output, cardiac index, aortic diameter, center line velocity of the blood through the aorta, and blood flow wave form. Slaved-in parameters include systemic vascular resistance (SVR) and arterial pressure. The monitor may be associated with a keypad (not shown) for entering patient parameters or may be pre-programmed with parameters such as body surface area (BSA), which is necessary to compute the cardiac index.

Figure 2:
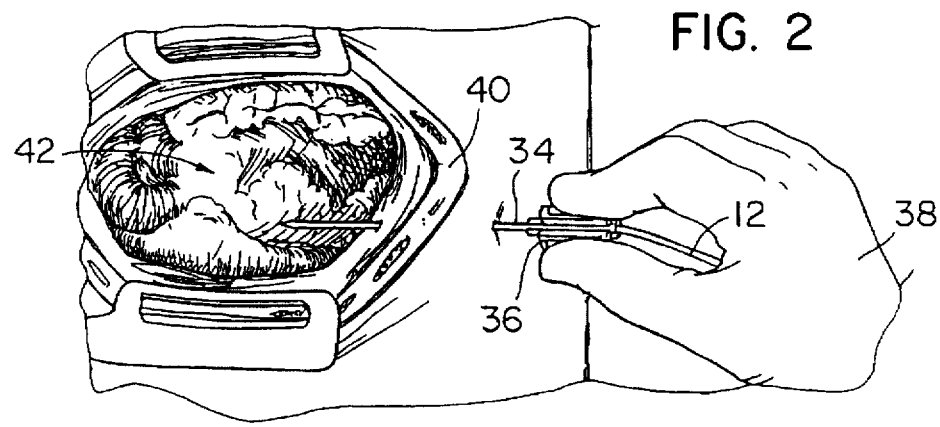
FIG. 2 is a top view of an exposed heart of a patient during open heart surgery and illustrating insertion of the cardiac monitoring catheter of FIG. 1.
Figure 3:
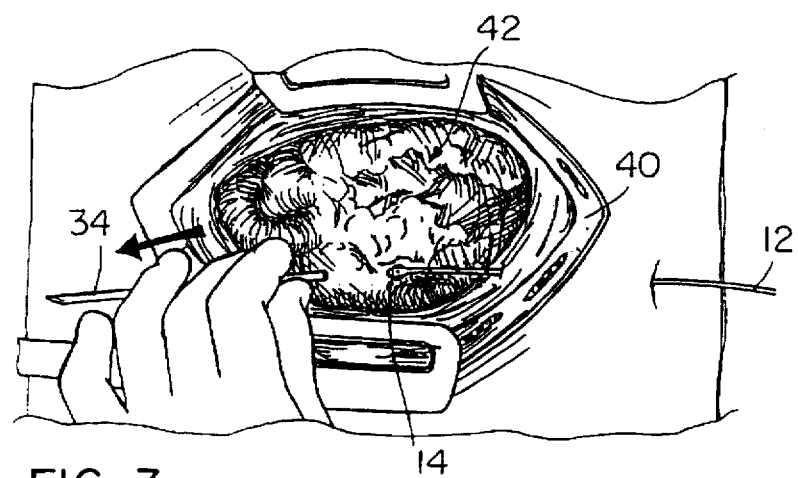
FIG. 3 is a view similar to FIG. 2 showing the catheter tip exposed for positioning behind the ascending aorta.
Figure 4:
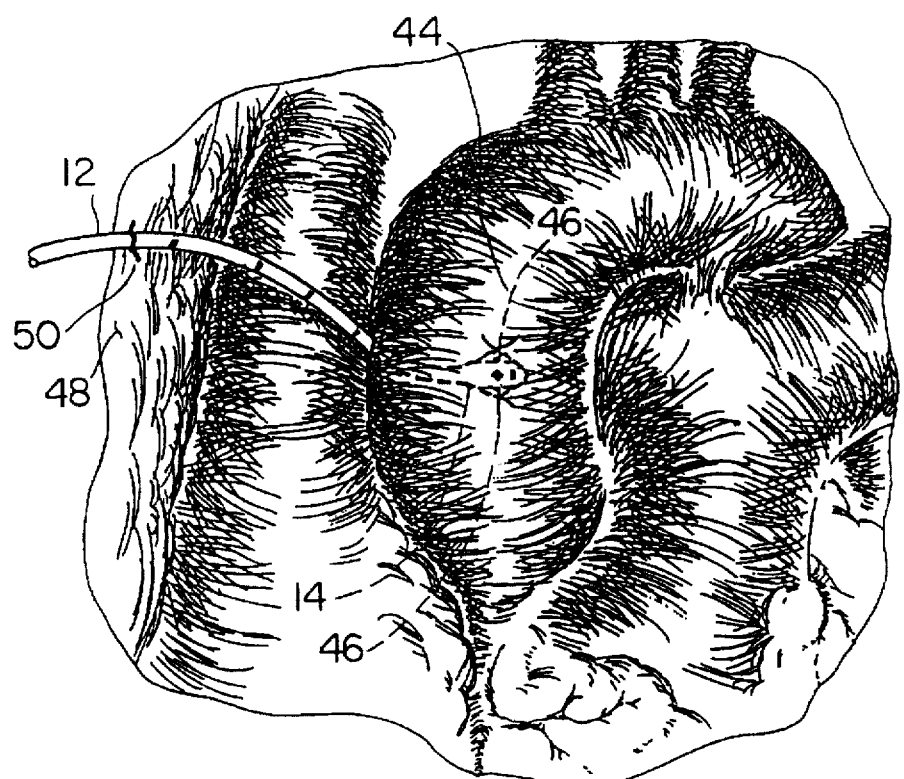
FIG. 4 is an enlarged view of the exposed heart showing placement of the cardiac monitoring catheter.
Figure 5:
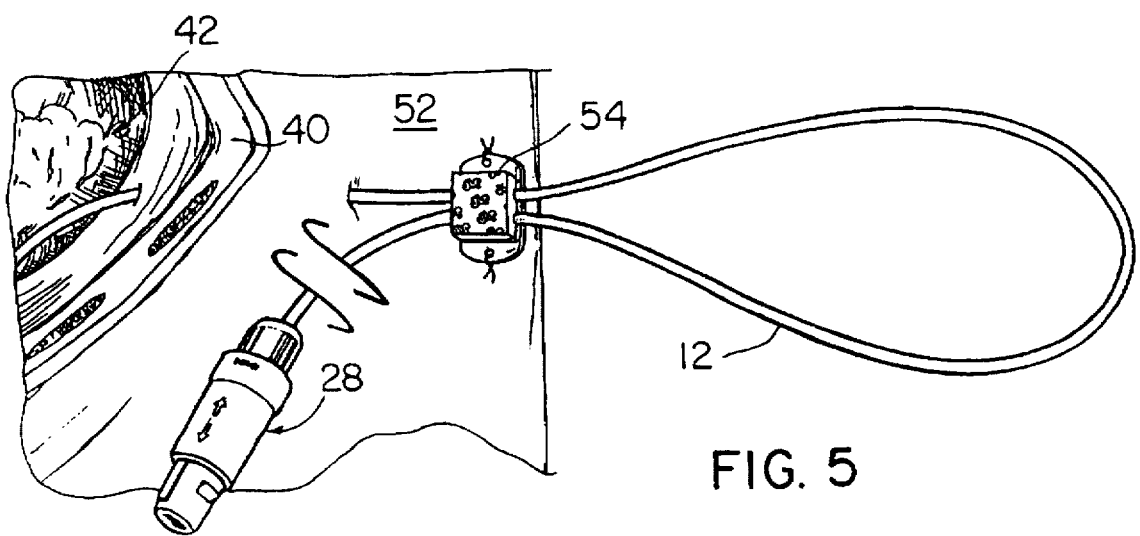
FIG. 5 is an enlarged view of the catheter trailing end secured to the patient's outer epidermis layer.

FIGS. 2-5 show the process for mounting the probe 14 in a patient. First, the probe 14 and wings 22 are received telescopically within a hollow needle 34, such as the DLP Scabbard™ Needle having an inserter or grip 36 provided thereon. The flexibility of the wings 22 permit them to be wrapped around the probe 14 when positioned in the needle 34. In use, the grip 36 is grasped by a surgeon's hand and the needle 34 with the attached catheter 10 are inserted through the chest wall 40 of a patient and into the open mediastinum 42, as seen in FIG. 2. Once the needle 34 and at least a portion of the catheter body 12 have been inserted through the chest wall, the needle 34 is separated from the catheter body 12, as seen in FIG. 3. In order to effectively determine cardiac output, the probe head 14 must be accurately positioned within the mediastinum 42. Preferably, the probe head 14 is positioned in the transverse sinus, behind the ascending aorta 44 and close to the aortic valve, as seen in FIG. 4. In this position, accurate readout of cardiac output is easily and safely obtained. The weight and anatomical position of the aorta alone lends itself to holding the probe head 14 securely in place. However, it is preferred that the probe head 14 be additionally secured to the posterior pericardial reflection with two 7-0sutures 46 placed through the suture ports 24 in the winged projections 22. Securing the probe head 14 in this fashion prevents the probe head from shifting while in use and permits easy and safe post-operative removal. The remaining catheter body 12 is secured to the lateral pericardial wall 48 using absorbable sutures 50 similar to an LA line securing technique. The sutures 50 act as a guide for the catheter when being removed, to prevent interference between the catheter and any vein grafts or cardiac structures. The catheter body 12 is then secured to the outer epithelial layer 52 of the chest wall 40 using a catheter anchoring collar 54, as seen in FIG. 5. The collar 54 may be secured to the epithelial layer 52 either through adhesive, tape, or sutures.

In order to remove the catheter 10, the anchoring collar 54 is first removed from the outer epithelial layer 52. The surgeon then simply pulls on the catheter body 12 until the 7-0 sutures 46 separate. This eliminates the need for a suture severing mechanism and prevents possible damage to the aorta as in the prior art. As the catheter 10 is withdrawn through the chest wall 40, the catheter body 12 and probe head 14 are guided around the pericardium 48 by the guide sutures 50, thereby keeping the catheter from snagging any vein grafts or cardiac structures. The catheter 10 is preferably removed from the closed mediastinum 24–72 hours post-operatively, prior to the removal of any chest tubes associated with the open heart surgery.

Unlike the prior art devices, the catheter 10 of the present invention can be inserted and positioned in the surgical patient immediately after mediansternotomy and division of the pericardium. In most cases the catheter 10 can be in position and operational in a matter of three to five minutes after skin incision. The catheter is inserted across the chest wall, into the open mediastinum and quickly positioned and secured in the transverse sinus under direct visualization. Once in position, baseline hemodynamic parameters can be obtained immediately by the anesthesiologist. The catheter 10 remains in position and out of the way during the surgical procedure. As the surgical repairs are completed, the catheter can resume functioning immediately as the patient is withdrawn from cardiopulmonary bypass, giving the surgical team a real-time picture of returning cardiac function. The prior art catheters cannot be positioned or used until the mediastinum is ready to be closed. In using the catheter 10 according to the invention, the anesthesiologist can utilize a CVP line (a current standard of practice) to administer fluids and pharmaceuticals. The catheter 10 can also be used in conjunction with a T-D catheter as well as an LA line on extremely critical patients.

Because the catheter 10 is not used intravascularly, this invention eliminates most of the problems and their related costs associated with T-D catheters. The catheter 10 according to the invention is more cost effective to operate and use as it does not require any operation other than an on/off switch. The catheter 10 of the present invention thus provides a level of accuracy and reliability far exceeding that of a T-D catheter without any of the related risks, side effects and resultant costs.

Reasonable variation and modification are possible within the spirit of the foregoing specification and drawings without departing from the scope of the invention.

The embodiments for which an exclusive property or privilege is claimed are defined as follows:

1. A system for continuously monitoring the output of a heart in a surgical patient, comprising:

a catheter having a proximal end and a distal end, the proximal end being adapted for electrical connection to a display;

a probe head provided on the catheter, the probe head including a probe and a pair of flexible flat projections extending outwardly from opposite sides of the probe for securing the probe head in the transverse sinus of the patient, each of the flexible projections having an outer edge portion;

at least one transducer positioned in the probe for detecting a condition of the heart; and a hollow needle adapted for receiving the probe head prior to installing the probe head in the patient, an inner diameter of the hollow needle being smaller than the distance between the outer edge portions of the flexible projections;

whereby the probe head can be installed in the patient immediately after mediansternotomy and division of the patient's pericardium by inserting the needle through the patient's chest wall.

2. A system according to claim 1 wherein the projections are wrapped around the probe when the probe head is received within the needle.

3. A system according to claim 1 wherein each projection includes an aperture for receiving at least one suture for anchoring the probe head against movement with respect to the body of a patient.

4. A system according to claim 1 wherein the projections and the probe together form a cobra head shape.

5. A system according to claim 1 and further in combination with the body of a patient having an ascending aorta, a transverse sinus located behind the aorta, and an aortic valve located adjacent the ascending aorta, and further wherein the probe head is adapted to be positioned in the transverse sinus behind the ascending aorta and in proximity to the aortic valve.

6. A combination according to claim 5 and further comprising a pericardial reflection posterior of the ascending aorta, and wherein the probe head is adapted to be sutured to the pericardial reflection.

7. A combination according to claim 6 wherein each projection includes an aperture for receiving at least one suture for anchoring the probe head to the pericardial reflection.

8. A combination according to claim 7 wherein the at least one transducer is oriented in the probe for measuring at least one of a centerline velocity of blood passing through the aorta and a change in diameter of the aorta during heart beating.

9. A system for continuously monitoring the output of a heart in a surgical patient, comprising:

a catheter having a proximal end and a distal end, the proximal end being adapted for electrical connection to a display;

a probe head provided on the catheter, the probe head including a probe and a pair of flexible wings extending outwardly from opposite sides of the probe for securing the probe head in the transverse sinus of the patient;

at least one transducer positioned in the probe for detecting a condition of the heart; and a hollow needle adapted for receiving the probe head prior to installing the probe head in the patient, the wings of the probe head being wrapped around at least a portion of the probe when the probe head is received within the needle;

whereby the probe head can be installed in the patient immediately after mediansternotomy and division of the patient's pericardium by inserting the needle through the patient's chest wall.

10. A system according to claim 9 wherein each projection includes an aperture for receiving at least one suture for anchoring the probe head against movement with respect to the body of a patient.

11. A system according to claim 9 wherein the projections and the probe together form a cobra head shape.

12. A system according to claim 9 and further in combination with the body of a patient having an ascending aorta, a transverse sinus located behind the aorta, and an aortic valve located within the ascending aorta, and further wherein the probe head is adapted to be positioned in the transverse sinus behind the ascending aorta and in proximity to the aortic valve.

13. A combination according to claim 12 and further comprising a pericardial reflection posterior of the ascending aorta, and wherein the probe head is sutured adapted to be to the pericardial reflection.

14. A combination according to claim 13 wherein each projection includes an aperture for receiving at least one suture for anchoring the probe head against movement to the pericardial reflection.

15. A combination according to claim 14 wherein the at least one transducer is oriented in the probe for measuring at least one of a centerline velocity of blood passing through the aorta and a change in diameter of the aorta during heart beating.

* * * * *